(12) United States Patent
Ljung et al.

(10) Patent No.: US 12,144,656 B2
(45) Date of Patent: Nov. 19, 2024

(54) PERSONAL HEALTH MONITORING

(71) Applicant: Sony Corporation, Tokyo (JP)

(72) Inventors: Rickard Ljung, Helsingborg (SE); Claes Nilsson, Lund (SE); Peter Karlsson, Lund (SE); Torbjörn Grahm, Malmö (SE)

(73) Assignee: Sony Corporation, Tokyo (JP)

(*) Notice: Subject to any disclaimer, the term of this patent is extended or adjusted under 35 U.S.C. 154(b) by 576 days.

(21) Appl. No.: 16/759,618

(22) PCT Filed: Nov. 22, 2017

(86) PCT No.: PCT/EP2017/080133
§ 371 (c)(1),
(2) Date: Apr. 27, 2020

(87) PCT Pub. No.: WO2019/101310
PCT Pub. Date: May 31, 2019

(65) Prior Publication Data
US 2020/0281536 A1   Sep. 10, 2020

(51) Int. Cl.
*A61B 5/00* (2006.01)
*G08B 21/04* (2006.01)
(Continued)

(52) U.S. Cl.
CPC .......... *A61B 5/7246* (2013.01); *A61B 5/7425* (2013.01); *G08B 21/0453* (2013.01);
(Continued)

(58) Field of Classification Search
None
See application file for complete search history.

(56) References Cited

U.S. PATENT DOCUMENTS 10,898,075 B2 * 1/2021 Miller .................... G16H 40/67
11,026,613 B2 * 6/2021 Cronin ................... A61B 5/746
(Continued)

FOREIGN PATENT DOCUMENTS

WO   2016/110804 A1   7/2016
WO   2016/164485      10/2016

OTHER PUBLICATIONS

International Search Report and Written Opinion for corresponding Patent Application No. PCT/EP2017/080133 dated Jul. 2, 2018.

*Primary Examiner* — Shirley X Jian
(74) *Attorney, Agent, or Firm* — Renner, Otto, Boisselle & Sklar, LLP

(57) ABSTRACT

A method for personalized monitoring of a user's health, e.g. on a personal electronic device, optionally in combination with a computing device. The method obtains (32) sensor data from one or more sensors associated with the user and generates (33), based on the sensor data, measurement values of a primary parameter. The method further identifies (31), among a default set of secondary parameters, one or more selected secondary parameters which, for the user, are found to correlate with the primary parameter. The method may further generate (34), based on the sensor data, measurement values of the selected secondary parameter(s) so as to selectively provide measurement values that are relevant for the health of the user as monitored by the primary parameter. Alternatively or additionally, the method may present the selected secondary parameter(s) to the user to inform the user about relevant secondary parameter(s).

14 Claims, 4 Drawing Sheets

(51) Int. Cl.
    *G16H 40/67* (2018.01)
    *G16H 50/20* (2018.01)
    *G16H 50/30* (2018.01)
    *G16H 50/70* (2018.01)
    *A61B 5/0205* (2006.01)
    *A61B 5/021* (2006.01)
    *A61B 5/024* (2006.01)
    *A61B 5/08* (2006.01)
    *A61B 5/11* (2006.01)
    *A61B 5/145* (2006.01)
    *A61B 5/369* (2021.01)
    *G08B 21/18* (2006.01)

(52) U.S. Cl.
    CPC ............. *G16H 40/67* (2018.01); *G16H 50/20* (2018.01); *G16H 50/30* (2018.01); *G16H 50/70* (2018.01); *A61B 5/0205* (2013.01); *A61B 5/02055* (2013.01); *A61B 5/021* (2013.01); *A61B 5/02405* (2013.01); *A61B 5/0816* (2013.01); *A61B 5/1112* (2013.01); *A61B 5/1117* (2013.01); *A61B 5/14532* (2013.01); *A61B 5/14542* (2013.01); *A61B 5/369* (2021.01); *A61B 5/4266* (2013.01); *A61B 5/4818* (2013.01); *A61B 5/4866* (2013.01); *A61B 5/746* (2013.01); *G08B 21/182* (2013.01)

(56) References Cited

U.S. PATENT DOCUMENTS

| | | | |
|---|---|---|---|
| 2008/0162088 A1* | 7/2008 | DeVaul | A61B 5/7264 |
| | | | 702/189 |
| 2015/0051451 A1* | 2/2015 | Kido | G06Q 10/04 |
| | | | 600/595 |
| 2015/0238139 A1* | 8/2015 | Raskin | A61B 5/4809 |
| | | | 600/595 |
| 2016/0034663 A1* | 2/2016 | Nino | G16H 10/60 |
| | | | 705/2 |
| 2018/0056130 A1* | 3/2018 | Bitran | A63B 24/0075 |
| 2018/0107793 A1* | 4/2018 | Ni | G16H 20/00 |
| 2018/0116607 A1* | 5/2018 | Yu | A61B 5/681 |
| 2018/0310867 A1* | 11/2018 | Sivan | A61B 5/165 |
| 2019/0282178 A1* | 9/2019 | Volosin | A61B 5/0022 |

* cited by examiner

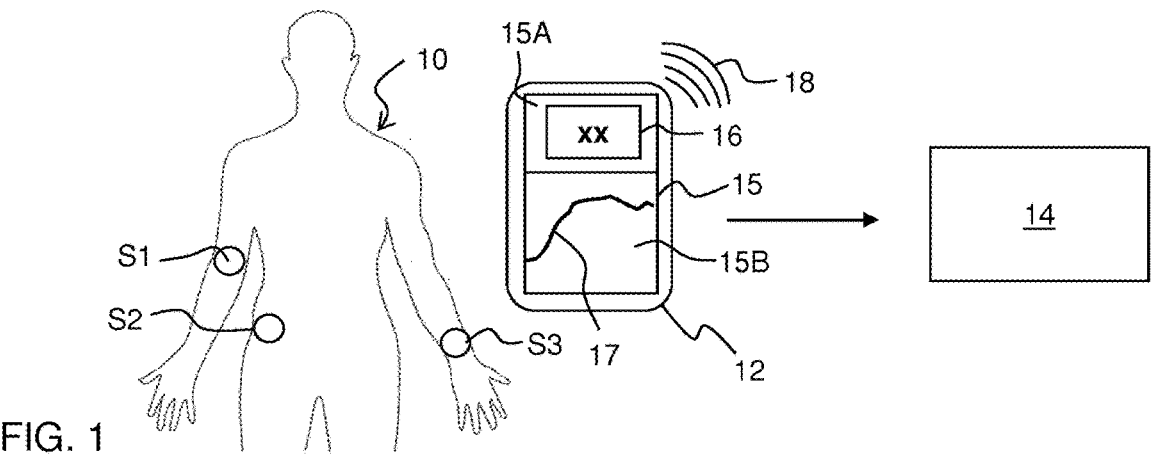
FIG. 1
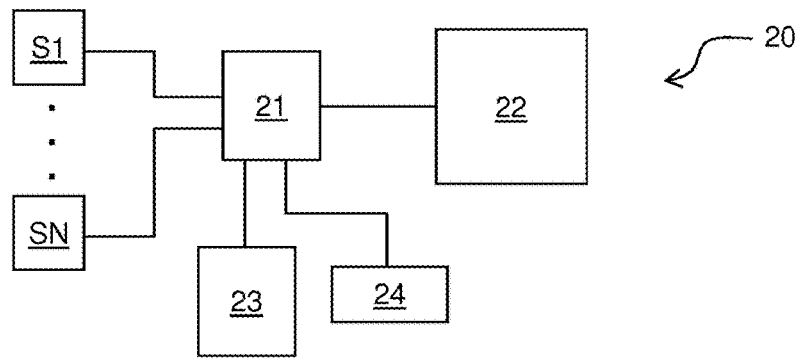
FIG. 2
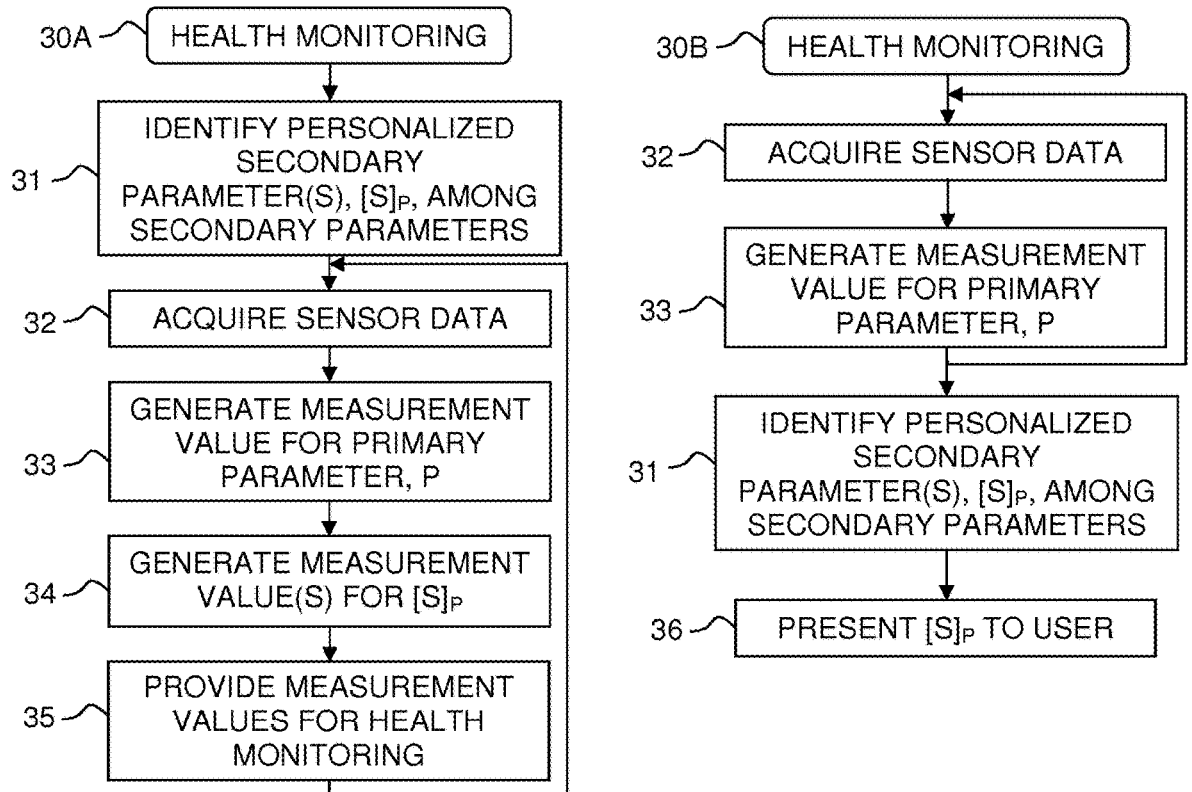
FIG. 3A
FIG. 3B

PERSONAL HEALTH MONITORING

TECHNICAL FIELD

The present invention relates generally to systems and methods for monitoring an individual's health based on sensors associated with the individual, also known as personal health monitoring.

BACKGROUND

Personal health monitoring is a growing field and finds many applications, e.g. fitness tracking and medical surveillance to name a few. In personal health monitoring, a user's health may be monitored based on readings from one or more sensors worn by the user. The sensors may be integrated in a monitoring device worn by the user, e.g. a wristband, a watch, a pedometer, a fitness tracker, etc. Monitoring devices may also support external sensors, e.g. a chest strap with heart rate sensors, a cadence sensor, etc. Simple monitoring devices are only capable of measuring a single parameter. However, many monitoring devices are capable of monitoring and reporting multiple health-related parameters, such as position, step count, heart rate, blood glucose level, skin temperature, detected food intake (eating, drinking) and activities (e.g. running, sleeping), etc.

WO2016/164485 discloses an activity classification server that receives raw data from one or more activity-tracking devices worn by a user. The activity-tracking devices operate at a given sampling rate to provide the raw data. The server processes the raw data to classify the user's activities into one or more identifiable states. To optimize energy usage and thereby prolong battery life of the activity-tracking devices, the server adjusts the sampling rate of the activity-tracking devices based on the state of the user at any given time.

There is a continued need to optimize the performance of health monitoring devices, e.g. with respect to energy consumption and user experience.

SUMMARY

It is an objective of the invention to at least partly overcome one or more limitations of the prior art.

Another objective is to enable resource-efficient monitoring of an individual's health based on multiple measured health-related parameters.

A further objective is to improve the user experience during monitoring of an individual's health.

One or more of these objectives, as well as further objectives that may appear from the description below, are at least partly achieved by a method, a computer-readable medium, a portable electronic device, a computing device and a system according to the independent claims, embodiments thereof being defined by the dependent claims.

A first aspect of the invention is a method for monitoring a user's health based on one or more sensors that are associated with the user. The method comprises: obtaining sensor data from a set of sensors among the one or more sensors, and generating, based on the sensor data from the set of sensors, measurement values of a primary parameter. The method further comprises: identifying, among a default set of secondary parameters, one or more selected secondary parameters which, for the user, are found to correlate with the primary parameter.

A second aspect of the invention is a computer-readable medium comprising computer instructions which, when executed by a processor, cause the processor to perform the method of the first aspect or any of its embodiments.

A third aspect of the invention is a portable electronic device, which is configured for connection to one or more sensors that are associated with a user. The portable electronic device is configured to: obtain sensor data from a set of sensors among the one or more sensors; generate, based on the sensor data from the set of sensors, measurement values of a primary parameter; and identify, among a default set of secondary parameters, one or more selected secondary parameters which, for the user, are found to correlate with the primary parameter.

A fourth aspect of the invention is a computing device configured to communicate, over a communication network, with a portable electronic device in accordance with the third aspect. The computing device is configured to: receive, from the portable electronic device, measurement values of the default set of secondary parameters and measurement values of the primary parameter, which have been generated based on sensor data from at least one of the one or more sensors associated with the user; analyze the measurement values of the default set of secondary parameters and the measurement values of the primary parameter for identification of the one or more selected secondary parameters; and transmit an indication of the one or more selected secondary parameters to the portable electronic device.

A fifth aspect is a system for monitoring a user's health. The system comprises: one or more sensors associated with the user; a control module configured to obtain sensor data from a set of sensors among the one or more sensors, and generate, based on the sensor data from the set of sensors, measurement values of a primary parameter; and an analysis module configured to identify, among a default set of secondary parameters, one or more selected secondary parameters which, for the user, correlate with the primary parameter.

Other objectives, as well as features, aspects and advantages of embodiments of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIG. 1 is a block diagram of a system environment for health monitoring in accordance with an embodiment.

FIG. 2 is a block diagram of a system for health monitoring in accordance with an embodiment.

FIGS. 3A-3B are flow charts of methods for health monitoring in accordance with embodiments.

DETAILED DESCRIPTION OF EXAMPLE EMBODIMENTS

Figure 4:
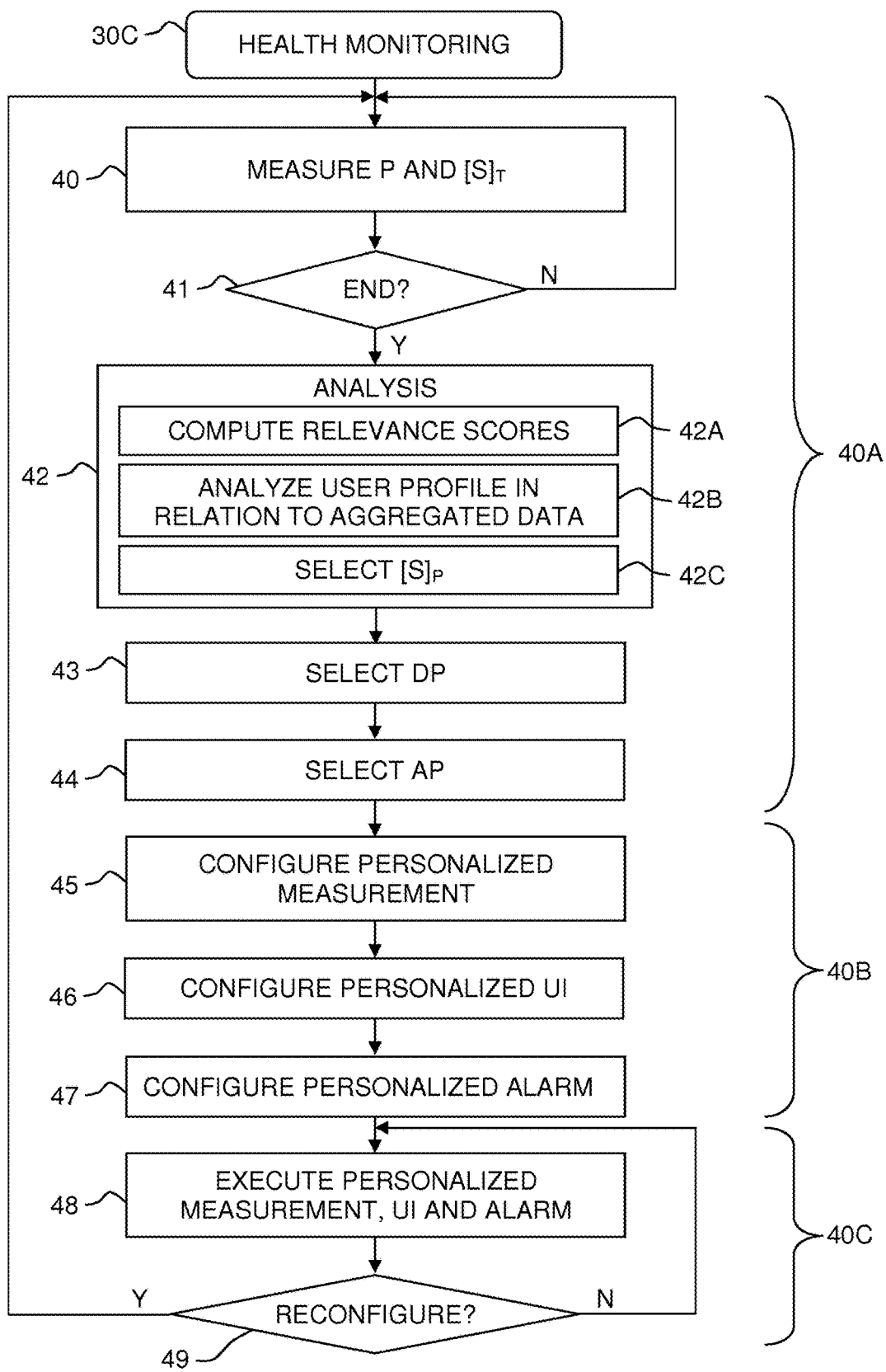
FIG. 4 is a flow chart of a method for health monitoring in accordance with a detailed embodiment.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Well-known functions or constructions may not be described in detail for brevity and/or clarity. Unless otherwise defined, all terms (including technical and scientific terms) used herein have the same meaning as commonly understood by one of ordinary skill in the art to which this invention belongs.

Before describing embodiments of the invention in more detail, a few definitions will be given.

As used herein, "health monitoring" refers to monitoring of the well-being of an individual in a general sense. The monitoring may aim at detecting or predicting an undesirable condition of the individual, e.g. occurrence of a known health problem or health issue of the individual, or occurrence of a potential health problem of the individual. Such a health problem may include any type of medical condition. Another example of an undesirable condition is that the individual falls to the ground. Alternatively, the health monitoring may aim at estimating or verifying a desirable condition, e.g. a fitness level.

As used herein, a "sensor" refers to any device that may be associated with an individual and is configured to measure a quantity related to the individual, in a broad sense. Non-limiting examples of sensors include accelerometers, gyroscopes, altimeters, pedometers, vibration sensors, blood glucose sensors, blood pressure sensors, skin temperature sensors, ambient temperature sensors, pupil size sensors, pulse oximeters, heart rate monitors, global positioning systems (GPS), sweat sensors, moisture sensors, insulin level detectors, and bioelectric current sensors.

A sensor may be "associated with" an individual by being worn by the individual, e.g. attached to the individual's body or clothing or implanted into the individual's body, or by being located in proximity of the individual in a monitoring situation. In one example, the sensor is included in a wearable or portable device, such as a fitness monitor, a wristband, a chest strap, a helmet, headphone, a mobile phone, an action camera, an adhesive patch, eyeglasses, a hearing aid, etc. In another example, the sensor is installed in the same building or room as the user, in a bed or in an exercise device.

As used herein, a "set" of items is intended to imply a provision of one or more items. Thus, a "set of sensors" may designate a single sensor or multiple sensors. Likewise, a "set of parameters" may designate a single parameter or multiple parameters.

As used herein, a "primary parameter" is any mandatory parameter that has been predefined to enable detection of a specific undesirable or desirable condition of the individual. In other words, the primary parameter is linked to the main purpose of the health monitoring. To give a few non-limiting examples, the primary parameter may be blood glucose level when the monitoring is aimed at detecting or predicting hypoglycemia, heart rate when the monitoring is aimed at detecting or predicting a heart disease or cardiac arrest, body orientation when the monitoring is directed to detecting or predicting a fall of the individual, and heart rate or heart rate variability when the monitoring is aimed at determining the fitness level of the individual. Although all examples herein involve health monitoring based on a single primary parameter, it is also conceivable that the health monitoring is based on more than one primary parameter.

As used herein, a "secondary parameter" is any parameter other than the primary parameter that may be monitored or calculated based on the monitoring and may be of potential relevance in the specific monitoring context. Thus, secondary parameters are optional parameters that may be monitored to supplement the primary parameter, e.g. to enable or improve prediction of the undesirable or desirable condition of the individual.

Each of the primary and secondary parameters may be defined by raw data from one sensor, or refined data derived by processing the raw data from one or more sensors. Each of the primary and secondary parameters may represent physiological or biometric data, motion data, position data, orientation data, etc. Examples of primary and secondary parameters include, without limitation, heart rate, speed, acceleration, angular velocity, orientation, position, blood glucose level, blood pressure, breathing rate, skin temperature, moisture, sweat rate, oxygen saturation, insulin level, bioelectric current, energy consumption, step count, body motion, brain activity, muscle motion, activity index, stress index, food intake index, resting index, snoring index, etc.

As used herein, "multiple regression" or "multiple regression analysis" is given its ordinary meaning and refers to a process for estimating relationships among variables. The focus of multiple regression may be to determine the relationship between a response variable (also known as criterion variable) and a number of predictor variables, specifically to parameterize a regression function which relates the response variable to the predictor variables and which may be linear or non-linear. As is well-known in the art, multiple regression comprises an optimization of the regression function based on observations of the response and predictor variables, and results in regression coefficients of the regression function. As also well-known in the art, multiple regression analysis may involve computing the statistical significance of the individual regression coefficients, e.g. so-called p-values, based on a hypothesis test.

Some embodiments of the invention relate to a technique for monitoring the health of an individual or user based on measurement values of a primary parameter. In accordance with some embodiments, the technique is personalized for the individual to the extent that the technique provides, for the health monitoring, measurement values of a personalized set of secondary parameters, which are selected among a default set of available secondary parameters based on their correlation with the primary parameter, and thereby their relevance for the current health monitoring of the individual. The personalized set is typically a subset of the default set. This means that the personalized technique may be designed to only generate measurement values for a subset of the available secondary parameters, while ensuring that the measurement values are relevant to the health monitoring by the primary parameter, e.g. for predicting the primary parameter. In another example the personalized technique may be designed to prioritize measurements for a subset of the available secondary parameters, e.g. in scenarios when there is a need to reduce the energy consumption or data transmission at a monitoring device. In practice, the technique is executed on or more electronic devices. It is realized that the personalization will save resources on the electronic device(s), e.g. processing power, by reducing the number of secondary parameters. The personalization may also save resources whenever it excludes, from the personalized set, a secondary parameter that is costly to generate in terms of processing power, e.g. by involving many computations or by requiring the measurement values to be generated at high sampling rate. Further, to the extent that the measurement values are transmitted between devices, the personalization will also reduce the required bandwidth of the transmission channel and/or decrease the transmission time. The personalization may also facilitate prediction of the primary parameter based on the measurement values of the personalized set of secondary parameters, since the secondary parameters in the personalized set have been selected based on their correlation with the primary parameter. Thus, the functional relation between the primary parameter and the personalized set of secondary parameters may be known, or can at least be efficiently computed.

The personalization may also have the additional technical advantage of facilitating selection of one or more relevant secondary parameters to be visualized to the individual, e.g. on a display, to improve the individual's understanding of how to avoid an undesirable condition or achieve an desirable condition, whatever is relevant.

The personalization may also have the additional technical advantage of enabling personalized alarms based on one or more relevant secondary parameters, e.g. to alert the individual that an undesirable condition is approaching and allowing the individual to take countermeasures.

In accordance with some embodiments, the technique is personalized for the individual to the extent that the technique identifies and presents the personalized set of secondary parameters to the user, thereby allowing the user to gain an understanding about the secondary parameters that are (most) relevant for the primary parameter and thus the health monitoring.

In summary, the personalization in accordance with embodiments of the invention may reduce energy consumption and/or improve performance and/or improve user experience.

FIG. 1 illustrates an implementation example of personal health monitoring in accordance embodiments of the invention. An individual 10 is provided with a number of sensors S1-S3. In the illustrated example, sensor S1 is worn on the upper arm, S2 is worn at the hip, and S3 is worn on the wrist. The sensors S1-S3 provide respective sensor data. The sensor data is acquired by a portable electronic device 12, designated PED in the following. The PED 12 may be any electronic device which is capable of being carried, held or worn by a user. For example, the PED 12 may be a handheld device, such as a mobile phone, smartphone, tablet, laptop, etc, as well as a wearable computer ("wearable"). The PED 12 may be a generic device capable of performing different tasks, e.g. by executing different application programs, or a specialized device tailored to perform a single specific task.

As will described in greater detail below, the PED 12 is a personal monitoring device that generates, based on the sensor data from the sensors S1-S3 or a subset thereof, measurement values of a primary parameter and a personalized set of secondary parameters. As shown, the PED 12 may be further configured to report the measurement values to a computing device 14, which is configured to perform a remote health monitoring, e.g. by storing the measurement values, by displaying the measurement values, by analyzing the measurement values for identification of trends or for prediction, by generating alarms or alerts for monitoring personnel such as caretakers, medical staff, clinical experts, etc. Alternatively or additionally, the PED 12 may be configured perform a local health monitoring, e.g. by storing the measurement values, displaying health-related data or generating an alarm when certain measurement values fulfill an alarm criterion. In the illustrated example, the PED 12 is configured to define a user interface (UI) 15 for displaying measurement values of the primary parameter, e.g. in a first UI section or window 15A, and measurement values of one or more secondary parameters, e.g. in a second UI section or window 15B. The measurement values may be displayed in plain text, as indicated by 16, or graphically, as indicated by 17. In the illustrated example, the PED 12 is also operable to selectively generate an alarm signal 18.

FIG. 2 is a block diagram of a system 20 for personal health monitoring in accordance with an embodiment. The system 20 may be implemented in the context of FIG. 1. The system 20 comprises a number of sensors S1-SN, with N≥1. A control module 21 is connected to the sensors S1-SN and configured to selectively acquire sensor data from the sensors. The control module 21 is further configured to selectively generate measurement values of primary and secondary parameters based on the sensor data. The control module 21 is further connected to an analysis module 22, which is operable to analyze measurement values received from the control module 21 for determination of the personalized set of secondary parameters for the specific individual that is being monitored. The control module 21 is further connected to a display module 23 and an alarm module 24. The display module 23 may be configured by the control module 21 to display a personalized user interface (cf. 15 in FIG. 1). The alarm module 24 may be operable by the control module 21 to generate an alarm signal (cf. 18 in FIG. 1).

The system 20 of FIG. 2 may be partitioned onto physical devices in different ways. In one extreme, all components of the system 20 are arranged in physically separated devices, such that the sensors S1-SN are physically separated from each other and from the modules 21-24, which also are physically separated from each other. In another extreme, the sensors S1-SN and the modules 21-24 are all arranged in a single physical device, e.g. the PED 12 in FIG. 1. Further examples are given below with reference to FIGS. 5A-5C.

Generally, the connections between components in the system 20 of FIG. 2 may be implemented by wired or wireless data transmission, based on any suitable communication protocol known in the art.

FIG. 3A illustrates a method 30A for personal health monitoring in accordance with an embodiment. With reference to the system 20 in FIG. 2, the method 30A may be executed by the control module 21. Step 31 identifies, among a default set of secondary parameters, one or more selected secondary parameters that are found to correlate with the primary parameter, designated P in the following. The selected secondary parameter(s) define the personalized set of secondary parameters, designated $[S]_P$ in the following. The personalized set $[S]_P$ is typically a subset of the default set of secondary parameters, designated $[S]_T$ in the following. The default set $[S]_T$ may be given by a default configuration of the control module 21, and the generation of measurement values for the secondary parameters in $[S]_T$ is enabled by hardware circuitry and/or computation algorithms in the control module 21.

In step 31, the control module 21 may identify $[S]_P$ by generating and transmitting measurement values of P and $[S]_T$ to the analysis module 22, which thereby returns an indication of $[S]_P$ to the control module 21. The corresponding process for determining $[S]_P$ in the analysis module 22 will be exemplified below with reference to FIG. 4. By step 31, the control module 21 acquires an individual configuration for use in a subsequent monitoring phase, which is represented by a repeating sequence of steps 32-35 in FIG. 3. In step 32, sensor data is acquired from one or more of the sensors S1-SN. In step 33, a measurement value for the primary parameter is generated based on the sensor data. In step 34, a measurement value is generated for the respective secondary parameter in $[S]_P$. In step 35, the measurement values may be provided for health monitoring, which may be performed as described in relation to FIG. 1.

It should be understood that step 32 may acquire sensor data at any desired sampling rate and from a monitored set of sensors that may include any sensor or combination of sensors among sensors S1-SN. The monitored set of sensors is given by the secondary parameter(s) that are included in the personalized set $[S]_P$. Further, steps 33 and 34 may be implemented to generate the measurement values of the respective parameter at an individual sampling rate. The sampling rate for the respective parameter may be either predefined or dynamically determined, e.g. as described in above-mentioned WO2016/164485.

FIG. 3B illustrates a method 30B for personal health monitoring in accordance with an embodiment. With reference to the system 20 in FIG. 2, the method 30B may be executed by the control module 21. The method 30B involves a monitoring phase comprising a repeating sequence of steps 32 and 33, which acquire sensor data and generate measurement values for the primary parameter P, as described hereinabove. Although not shown in FIG. 3B, the monitoring phase may also provide the measurement values of the primary parameter P for health monitoring (cf. step 35 in FIG. 3A). Subsequent to the monitoring phase, the method 30B proceeds to step 31 which, as described for FIG. 3A, identifies the personalized set $[S]_P$ of secondary parameters among the default set $[S]_T$ of secondary parameters. For example, in step 31, the control module 21 may identify $[S]_P$ by generating and transmitting measurement values of P and $[S]_T$ to the analysis module 22, which thereby returns an indication of $[S]_P$ to the control module 21. The method 30B then proceeds to step 36, which presents the secondary parameters in $[S]_P$ to the user, e.g. on the display module 23. The method 30B does not generate measurement values of the secondary parameter(s) in $[S]_P$, but enables the user to gain information about secondary parameter(s) that are of relevance to the primary parameter and the aim of the health monitoring.

FIG. 4 illustrates a method 30C for personal health monitoring in accordance with an embodiment. With reference to the system 20 in FIG. 2, the method 30C may be executed by the control module 21 and the analysis module 22 in combination. The method 30C involves an analysis phase 40A, a configuration phase 40B, and a monitoring phase 40C.

The analysis phase 40A comprises steps 40-44. By steps 40-41, measurement values are repeatedly generated for the primary parameter P and the secondary parameters in the default set $[S]_T$ for a predefined time period, resulting in time-sequences of measurement values. By analogy with steps 32-34 in FIG. 3A, step 40 involves acquiring sensor data and generating measurement values based on the sensor data. Step 40 may acquire the sensor data from all of the available sensors S1-SN, but it is conceivable that the sensor data is acquired from a subset thereof. The set of sensors that provide sensor data in step 40 may be given by a default configuration and may be denoted a "default set of sensors".

In step 42, the resulting measurement values are analyzed for identification of the one or more selected secondary parameters that define the personalized set $[S]_P$. The analysis in step 42 may comprise a sub-step 42A of computing a relevance score or priority for each secondary parameter in the default set $[S]_T$. The relevance score may indicate the relative impact of the secondary parameter on the primary parameter. The relevance score may be determined by operating any suitable analysis technique or data mining technique on the measurement values from steps 40-41. Many such techniques are readily available to the person skilled in the art. In one embodiment, the relevance score is indicative of a degree of correlation between the primary parameter and the respective secondary parameter. In one embodiment, step 42A performs a multiple regression analysis of the measurement values from step 40-41. The multiple regression analysis may comprise optimizing a regression function which has a response variable given by the primary parameter P and predictor variables given by the secondary parameters in the default set $[S]_T$. The relevance scores may then be generated as a function of the regression coefficients of the optimized regression function, and possibly also as a function of the statistical significance of the respective regression coefficient. For example, the relevance score for a parameter may be set in proportion to the magnitude of its regression coefficient, provided that the regression coefficient is deemed to be statistically significant. Parameters with regression coefficients that are deemed not to be statistically significant may be given a low relevance score.

Generally, in all embodiments disclosed herein, the analysis to identify the one or more selected secondary parameters that correlate with the primary parameter may be based on any conceivable algorithm or algorithms for this purpose, including but not limited to multiple regression analysis, machine-learning analysis, statistical analysis, or any similar estimation method, or any combination thereof.

The analysis in step 42 may further comprise a sub-step 42B that involves obtaining and analyzing a user profile for the individual 10, e.g. by use of big data analytics. The user profile may define one or more properties of the individual 10, such as age, gender, weight, height, BMI, medical history, country of residence, country of birth, ethnicity, etc. Sub-step 42B may further comprise comparing the user profile 10 to aggregated data for a larger population of individuals, where the aggregated data represents measurement values of primary and secondary parameters obtained for the larger population of individuals, which are associated with a respective user profile. The aggregated data may thereby indicate, directly or indirectly, that certain sets of secondary parameters are relevant for different user profiles, or for different values of one or more properties in the user profiles. Thus, sub-step 42B may match one or more properties of the individual, given by the user profile, to the aggregated data, so as to identify a set of secondary parameters that are likely to have a significant impact on the primary parameter, or even identify a likely order of relevance within such a set of secondary parameters. In such an implementation, sub-step 42B may be seen to assign a second relevance score to the respective secondary parameter in $[S]_T$.

The analysis in step 42 further comprises a sub-step 42C which may determine $[S]_P$ as a function of the output of sub-step 42A, and optionally as a function of the output of sub-step 42B. In one example, $[S]_P$ may be defined to include a predefined number of the secondary parameters that have the highest relevance score or all of the secondary parameters that have a relevance score above a predefined limit. In another example, the relevance scores from sub-step 42A may be modified, e.g. weighted, by the second relevance scores from sub-step 42B, so as to relatively increase the relevance score of the secondary parameters that are deemed by sub-step 42B to have a large relevance. In an alternative embodiment, sub-step 42C may identify $[S]_P$ only as a function of the output of sub-step 42B.

In a variant, the second relevance score from sub-step 42B may used for defining the regression function, e.g. to exclude certain secondary parameters. In such a variant, sub-step 42C will identify $[S]_P$ as a function of the output of sub-step 42A and, implicitly, as a function of the output of sub-step 42B.

Generally, it is conceivable that step 42 adds one or more secondary parameters to the default set $[S]_T$ and/or removes one or more secondary parameters from the default set $[S]_T$ as part of the analysis. For example, step 42 may combine one or more secondary parameters into a new secondary parameter, which thereby may be included in the personalized set $[S]_P$ depending on the outcome of the analysis.

Although not shown in FIG. 4, the analysis phase 40A may include a further step of determining a sampling rate for the primary parameter and/or one or more secondary parameters in the personalized set $[S]_P$, e.g. as described in WO2016/164485.

Step 43 selects at least one display parameter, DP, as a function of $[S]_P$ from step 42. The DP(s) may be selected based on the relevance scores, optionally weighted by the second relevance scores. In one example, step 43 may select the secondary parameter(s) with the highest relevance score or the secondary parameters that have a relevance score above a predefined limit. In another example, at least one DP may be a new parameter that is formed based on one or more of the secondary parameters in $[S]_P$.

Step 44 selects at least one alarm parameter, AP, as a function of $[S]_P$ from step 42. The AP(s) may be selected based on the relevance scores, optionally weighted by the second relevance scores. In one example, step 44 may select the secondary parameter(s) with the highest relevance score or the secondary parameters that have a relevance score above a predefined limit. In another example, at least one AP may be a new parameter that is formed based on one or more of the secondary parameters in $[S]_P$. Step 44 may also determine an appropriate alarm criterion, e.g. an alarm limit for the respective AP. The alarm criterion may be determined based on the above-mentioned aggregated data and/or the measurement values from steps 40-41.

The configuration phase 40B comprises steps 45-47. Step 45 configures a personalized measurement based on $[S]_P$ from step 42, so as to generate measurement values for P and $[S]_P$, at a respective sampling rate, during forthcoming step 48. Step 46 configures a display control function to provide a personalized UI for presentation of the measurement values of the DP(s), and optionally the measurement values of P, during forthcoming step 48. Step 47 configures a personalized alarm control function to monitor the AP(s) with respect to an alarm criterion, which may be predefined or determined by step 44 to indicate an alarm condition. Step 47 also configures the personalized alarm control function to generate an alarm signal when the alarm criterion is met.

The monitoring phase 40C comprises steps 48-49. Step 48 executes the personalized measurement of P and $[S]_P$, operates the display control function to present the measurement values of the DP(s) in the personalized UI, and operates the personalized alarm control function to monitor the measurement values of the AP(s) for an alarm condition. Step 48 may also provide the measurement values of P and $[S]_P$ for further remote or local monitoring, e.g. as described in relation to FIG. 1. Step 48 is repeated until step 49 detects a reconfiguration event, which causes step 49 to proceed to step 40 and thereby initiate the analysis phase 40A. In one example, the reconfiguration event is generated by a timer at regular time intervals, e.g. once a day, week or month. In another example, the reconfiguration event is generated on-demand by the individual, e.g. by the individual pushing in a button on the PED 12 in FIG. 1. In further examples, the reconfiguration event is generated if the number of alarms per unit time exceeds a limit, or based on statistical characteristics of the measurement values that are generated during step 48 for one or more parameters. For example, the reconfiguration may be generated if there is a significant and abrupt change in the measurement values.

In one embodiment of the system 20 in FIG. 2, the control module 21 is configured to perform steps 40-41 and steps 45-49, and the analysis module 22 is configured to perform steps 42-44. In such an embodiment, the control module 21 may provide the measurement values from steps 40-41 to the analysis module 22, which then returns an indication of the personalized set $[S]_P$, the AP(s) and the DP(s) to the control module 21. The analysis module 22 may also provide the relevance scores or a corresponding rating of the secondary parameters, the AP(s) or the DP(s) to the control module 21.

In another embodiment of the system 20 in FIG. 2, the control module 21 is configured to perform steps 40-41 and steps 43-49, and the analysis module 22 is configured to perform step 42. In such an embodiment, the control module 21 may provide the measurement values from steps 40-41 to the analysis module 22, which then returns an indication of the personalized set $[S]_P$ together with the relevance scores or a corresponding rating of the secondary parameters in $[S]_P$ to allow the control module 21 to determine the AP(s) and the DP(s).

To further exemplify the operation and advantages of the system 20 and the method 30, a non-limiting example will be given with reference to FIG. 1. In this example, the PED 12 has been produced to monitor and report status with respect to blood glucose level, which is thus the primary parameter. The blood glucose level may to a greater or lesser extent be dependent on other parameters, denoted secondary parameters herein. For example, the blood glucose value at a given time point could be a function dominated by the number of steps walked during the last hour before the given time point and the amount of food intake during the last 2 hours before the given time point. Hence, it may be possible to predict the expected future values of blood glucose level (primary parameter) by carefully measuring a selected set of secondary parameters. Further, the dependency of different secondary parameters could be different for different individuals. For example, a first individual may have a strong relationship between the primary parameter and a certain set of secondary parameters while a second individual may have a weak relationship between the primary parameter and the secondary parameters that are important for the first individual, but a strong relationship between the primary parameter and a set of other secondary parameters. Hence, there is a need to individually determine which secondary parameters the PED 12 should monitor in order to optimize the monitoring and prediction of the primary parameter. In one implementation example of FIG. 1, the individual 10 wears a sensor S1 capable of measuring the blood glucose level, a pedometer S2 capable of measuring number of walking steps, and a sensor S3 capable of measuring at least heart rate, skin temperature, blood pressure, skin moisture, GPS position, acceleration, angular velocity and orientation. Assuming that the PED 12 comprises modules 21-24 of system 20 (FIG. 2), the PED 12 may be configured to perform a health monitoring in accordance with FIG. 4 for the purpose of predicting and counteracting hypoglycemia in the individual 10. The PED 12 is configured to use the blood glucose level from sensor S1 as primary parameter and is operable, in a default configuration, to generate the following secondary parameters, which thus define the default set $[S]_T$: heart rate, skin temperature, blood pressure, skin moisture, number of walking steps per unit time, a food intake index (e.g. computed based on acceleration, orientation, angular velocity from sensor S3), an activity index (e.g. computed based on acceleration, GPS position, orientation, angular velocity from sensor S3 and number of walking steps from sensor S2), and a stress index (e.g. computed based on heart rate, blood pressure and skin moisture from sensor S3). The method executed by the PED 12 identifies, by step 42, a personalized set $[S]_P$ for the individual 10 with the following selected secondary parameters: heart rate, number of walking steps, activity index and food intake index, with the food intake index having the highest relevance score. The PED 12 then presents, in section 15A, the measured values of the blood glucose level and, in section 15B, the measured values of the food intake index. The PED 12 also monitors the food intake index and generates an alarm signal when the food intake index reaches a threshold value. For another individual which is equipped with the same system 20, the PED 12 instead identifies a personalized set $[S]_P$ with the following selected secondary parameters: activity index, blood pressure and food intake index, presents the activity index and the blood pressure as DPs in section 15B and monitors the activity index as an AP. Thus, even if the health monitoring targets the same primary parameter for the two individuals, the personalization may result in differences in the secondary parameters that are monitored, presented to the individual and result in alarm generation.

Figure 5A:
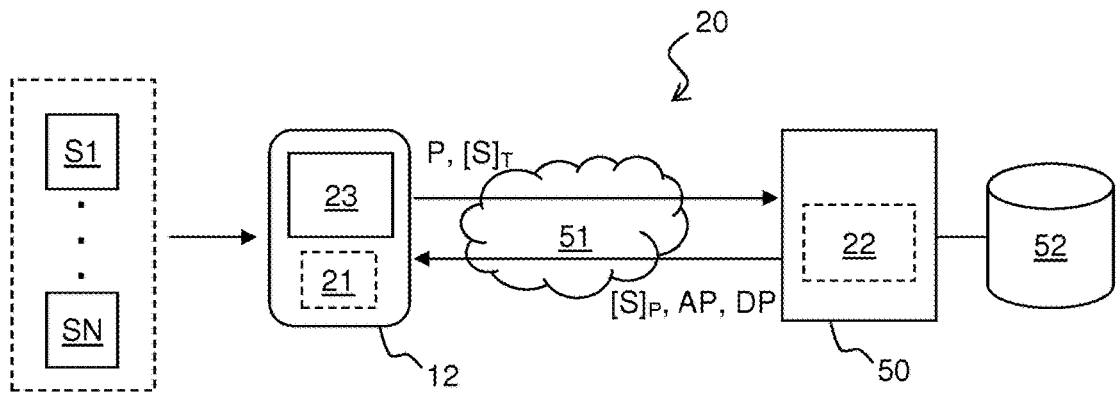
FIGS. 5A-5C are block diagrams of example implementations of the system in FIG. 2.
Figure 5B:
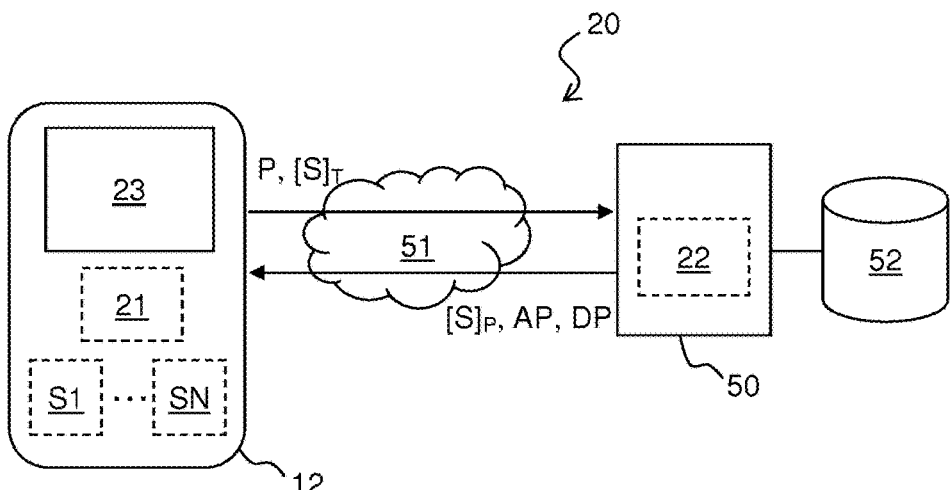
Figure 5C:
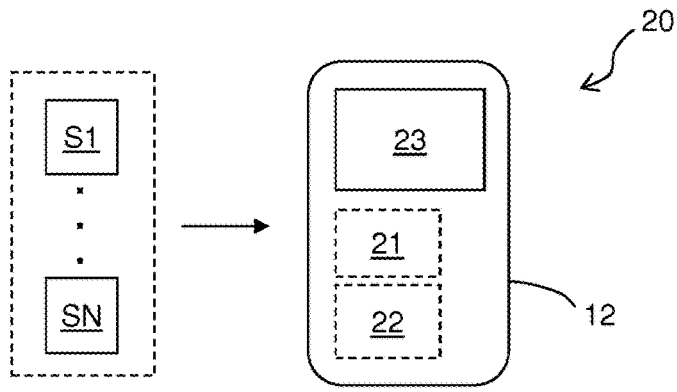

FIGS. 5A-5C exemplify implementations of the system 20 in FIG. 2. In all examples, the control module 21 uses a default configuration for measuring $[S]_T$ and reporting the measurement values to the analysis module 22, while the analysis module 22 conducts analytics on the reported data, e.g. big data analytics, multi-regression analytics, machine-learning analytics, statistical analytics or any similar estimation method for identifying significant secondary parameters. Once the analysis module 22 has identified the significant selection of secondary parameters for the specific user and determined an individual configuration, this individual configuration is transmitted to the control module 21, which adapts its measuring, reporting and display presentation scheme accordingly.

In the example of FIG. 5A, the sensors S1-SN are physically separated from the PED 12, which comprises the control module 21, the display 23 and possibly the alarm module 24 (not shown). The PED 12 is configured to communicate over a network 51 with a computing device 50, e.g. a remote server such as a cloud sever, which comprises the analysis module 22. The network 51 may comprise any combination of wide area and/or local area and/or personal area networks (WAN/LAN/PAN). The computing device 50 has access to a database 52, which may contain the user profile of the individual and the aggregated data. With reference to FIG. 1, the PED 12 is a personal monitoring device associated with the individual that is being monitored. As indicated in FIG. 5A, the PED 12 transmits, during the analysis phase 40A (FIG. 4), measurement values of the primary parameter P and the secondary parameters in the default set $[S]_T$ to the computing device 50 via network 51. This causes the computing device 50, by the analysis module 22, to determine the personalized set $[S]_P$ and transmit an indication of thereof to the PED 12 over the network 51. In the illustrated example, the computing device 50 also transmits an indication of the display and alarm parameters DP, AP. Although not shown in FIG. 5A, the PED 12 may be further configured to transmit, during the subsequent monitoring phase 40C, the measurement values of P and $[S]_P$ over the network 51 to a computing device for remote monitoring (cf. 14 in FIG. 1), which may or may not be identical to the computing device 50. It is realized that the personalization in accordance with embodiments of the invention reduces the need for processing in the PED 12 and improves the user experience for the individual being monitored. It is also realized that the amount of data transferred to the computing device 14 will reduced by the personalization.

Compared to FIG. 5A, the example in FIG. 5B differs by the sensors S1-SN being integrated in the PED 12, and the example in FIG. 5C differs by the analysis module 22 being integrated in the PED 12. Otherwise, the description of FIG. 5A is equally applicable to FIGS. 5B-5C.

Figure 6:
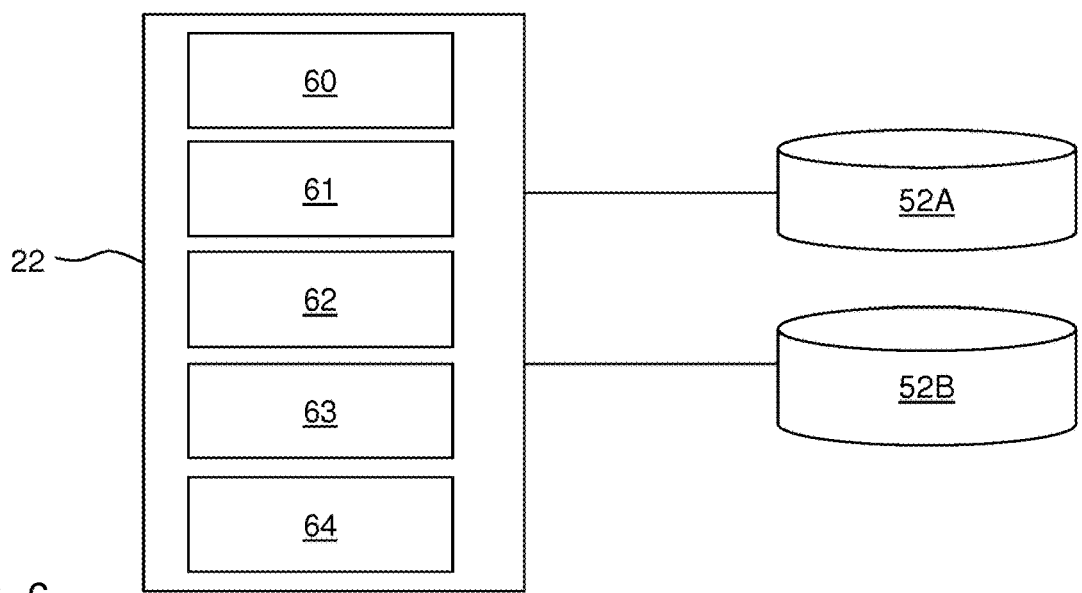
FIG. 6 is a block diagram of an analysis module in a system for health monitoring in accordance with an embodiment.

FIG. 6 is a block diagram of an analysis module 22 in accordance with an embodiment. The analysis module 22 comprises a statistical analysis module 60 which is configured to implement step 42A (FIG. 4), a profiling module 61 which is configured to implement step 42B, a reporting definition module 62 which is configured to implement 42C and outputs $[S]_P$, a UI configuration module 63 which is configured to implement step 44 and outputs DP, and an alarm configuration module 64 which is configured to implement 45 and outputs AP. As understood from the description of FIG. 4, the profiling module 61 may retrieve user profile data from a user profile database 52A and aggregated data from a population database 52B.

Figure 7:
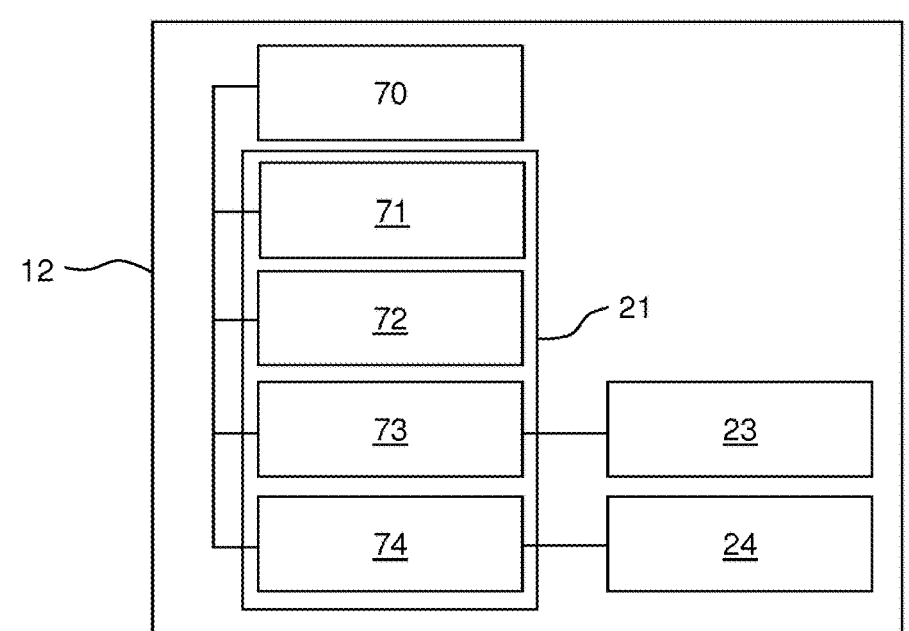
FIG. 7 is a block diagram of a local monitoring device in a system for health monitoring in accordance with an embodiment.

FIG. 7 is a block diagram of a PED 12 in accordance with an embodiment. The PED 12 comprises a communication module 70 which is configured to establish a communication channel, by wire and/or wirelessly, with the sensors S1-SN and the computing device 50 (FIGS. 5A-5B), and optionally with the computing device 14 (FIG. 1). The PED 12 further comprises a control module 21, a display module 23 and an alarm module 24. The control module 21 comprises a measurement controller 71 which is configured to implement steps 40-41 (FIG. 4) by retrieving sensor data, computing measurement values of $[S]_T$, and transmitting the measurement values to the analysis module 22. The measurement controller 71 is also configured to implement the monitoring phase 40C (steps 48-49). The control module 21 further comprises a reporting controller 72 which is configured to implement step 45 by configuring the measurement controller 71 to perform the monitoring phase 40C in accordance with $[S]_P$, a UI controller 73 which is configured to implement step 46, and an alarm controller 74 which is configured to implement step 47.

Figure 8:
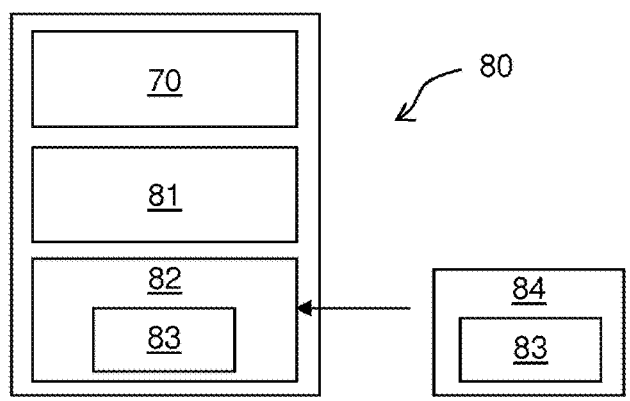
FIG. 8 is a block diagram of a machine that implements a local or remote monitoring device in accordance with an embodiment.

FIG. 8 is a diagrammatic representation of a machine 80 that may represent the PED 12 or the computing device 50. The machine 80 comprises a communication module 70 defining one or more interfaces for data communication in accordance with any suitable protocol or protocols. The machine 80 further comprises one or more processors 81, e.g. a central processing unit (CPU), a graphics processing unit (GPU), a digital signal processor (DSP), one or more application specific integrated circuits (ASICs), one or more radio-frequency integrated circuits (RFICs), a field programmable gate array (FPGA), or any combination thereof. The machine 80 further comprises system memory 82, which may include computer memory in the form of volatile and/or non-volatile memory such as read only memory (ROM), random access memory (RAM) and flash memory. The memory 82 may store computer instructions 83 (e.g. software or program code) for causing the machine 80 to perform any one of the methodologies discussed herein. The instructions 83 may be supplied to the machine 80 on a computer-readable medium 84, which may be a tangible (non-transitory) product (e.g. magnetic medium, optical medium, read-only memory, flash memory, digital tape, etc) or a propagating signal. When executed by the processor 81, the instructions 83 may cause the processor(s) 81 to perform any one of the methodologies discussed herein. In this context, it is to be understood that any of the modules described in the foregoing may be implemented by the processor(s) 81 executing the instructions 83. However, it is also conceivable that one or more of the modules are implemented solely by dedicated hardware in the machine 80.

The invention claimed is:

1. A method for monitoring a user's health condition based on one or more sensors that are associated with the user, said method comprising:
   obtaining sensor data from at least one computer-operable sensor of the one or more sensors,
   generating, based on the sensor data from the at least one computer-operable sensor, measurement values of a primary parameter associated with the user's health condition and being physiological or biometric data, the measurement values of the primary parameter being raw or refined sensor data obtained by the sensor,
   generating, based on the sensor data from the at least one computer-operable sensor, measurement values of a default set of secondary parameters related to the primary parameter and being physiological or biometric data, the measurement values of the default set of secondary parameters being raw or refined sensor data obtained by the sensor,
   analyzing the measurement values of the primary parameter and the measurement values of the default set of secondary parameters to determine a level of correlation of each secondary parameter of the default set of secondary parameters to the primary parameter,
   identifying, among the default set of secondary parameters, one or more personalized secondary parameters based on the respective level of correlation of each secondary parameter of the default set of secondary parameters with the primary parameter, and
   presenting the one or more personalized secondary parameters to the user on a display module for the user to monitor the user's health condition,
   wherein said analyzing comprises: computing a relevance score for each of the respective secondary parameters in the default set of secondary parameters, and identifying the one or more personalized secondary parameters as a function of the relevance score of each of the respective secondary parameters.

2. The method of claim 1, wherein said method further comprises generating, based on the sensor data from the at least one computer-operable sensor, measurement values of the one or more personalized secondary parameters.

3. The method of claim 1, wherein said analyzing comprises optimizing a regression function which has a response variable given by the primary parameter and predictor variables given by each of the secondary parameters in the default set of secondary parameters, and generating the relevance scores as a function of regression coefficients of the optimized regression function.

4. The method of claim 1, wherein said analyzing further comprises: obtaining a user profile for the user, comparing the user profile to aggregated data that represents measurement values of the primary and secondary parameters obtained for a population of individuals which are associated with a respective user profile, and identifying the one or more personalized secondary parameters based on said comparing.

5. The method of claim 1, further comprising: selecting at least one display parameter as a function of the one or more personalized secondary parameters, and configuring a display control function so that measurement values of the at least one display parameter are shown to the user on the display module.

6. The method of claim 1, further comprising: selecting at least one alarm parameter as a function of the one or more personalized secondary parameters, and configuring an alarm control function to generate an alarm signal based on measurement values of the at least one alarm parameter.

7. The method of claim 1, further comprising: providing at least one of the measurement values of the primary parameter and measurement values of each of the one or more personalized secondary parameters for said monitoring of the user's health.

8. A portable electronic device, which is configured for connection to one or more sensors that are associated with a user, the portable electronic device being configured to:
   obtain sensor data from at least one computer-operable sensor among the one or more sensors,
   generate, based on the sensor data from the at least one computer-operable sensor, measurement values of a primary parameter associated with a health condition of the user and being physiological or biometric data, the measurement values of the primary parameter being raw or refined sensor data obtained by the sensor,
   generate, based on the sensor data from the at least one computer-operable sensor, measurement values of a default set of secondary parameters related to the primary parameter and being physiological or biometric data, the measurement values of the default set of secondary parameters being raw or refined sensor data obtained by the sensor,
   analyze the measurement values of the primary parameter and the measurement values of the default set of secondary parameters to determine a level of correlation of each secondary parameter of the default set of secondary parameters to the primary parameter, identify, among the default set of secondary parameters, one or more personalized secondary parameters based on the respective level of correlation of each secondary parameter of the default set of secondary parameters with the primary parameter, and present the one or more personalized secondary parameters to the user on a display module for the user to monitor the user's health condition, wherein the portable electronic device is configured to analyze by: computing a relevance score for each of the respective secondary parameters in the default set of secondary parameters, and identifying the one or more personalized secondary parameters as a function of the relevance score of each of the respective secondary parameters.

9. The portable electronic device of claim 8, which is further configured to generate, based on the sensor data from the at least one computer-operable sensor, measurement values of the one or more personalized secondary parameters.

10. The portable electronic device of claim 8, which is configured to initiate the analysis by transmitting, over a communication network, the measurement values of the default set of secondary parameters and the measurement values of the primary parameter to a computing device which comprises an analysis module for identification of the one or more personalized secondary parameters, and wherein the portable electronic device is further configured to receive, from the computing device and over the communication network, an indication of the one or more personalized secondary parameters.

11. The portable electronic device of claim 8, which is further configured to initiate a selection of at least one display parameter as a function of the one or more personalized secondary parameters, and to cause measurement values of the at least one display parameter to be shown to the user on the display module.

12. The portable electronic device of claim 8, which is further configured to initiate a selection of at least one alarm parameter as a function of the one or more personalized secondary parameters, and to cause an alarm signal to be generated based on measurement values of the at least one alarm parameter.

13. A computing device configured to communicate, over a communication network, with a portable electronic device in accordance with claim 8, the computing device being configured to:

receive, from the portable electronic device, measurement values of the default set of secondary parameters and measurement values of the primary parameter, which have been generated based on sensor data from at least one of the one or more sensors associated with the user;

analyze the measurement values of the default set of secondary parameters and the measurement values of the primary parameter for identification of the one or more personalized secondary parameters; and transmit an indication of the one or more personalized secondary parameters to the portable electronic device.

14. A system for monitoring a user's health condition, comprising:

one or more sensors, including at least one computer-operable sensor, associated with the user;

a control module configured to:
  obtain sensor data from the at least one computer-operable sensor of the one or more sensors,
  generate, based on the sensor data from the at least one computer-operable sensor, measurement values of a primary parameter associated with the user's health condition and being physiological or biometric data, the measurement values of the primary parameter being raw or refined sensor data obtained by the sensor, and
  generate, based on the sensor data from the at least one computer-operable sensor, measurement values of a default set of secondary parameters related to the primary parameter and being physiological or biometric data, the measurement values of the default set of secondary parameters being raw or refined sensor data obtained by the sensor;

an analysis module configured to:
  analyze the measurement values of the primary parameter and the measurement values of the default set of secondary parameters to determine a level of correlation of each secondary parameter of the default set of secondary parameters to the primary parameter, and
  identify, among the default set of secondary parameters, one or more personalized secondary parameters which based on the respective level of correlation of each secondary parameter of the default set of secondary parameters with the primary parameter,
  wherein the control module is configured to analyze by computing a relevance score for each of the respective secondary parameters in the default set of secondary parameters, and identifying the one or more personalized secondary parameters as a function of the relevance score of each of the respective secondary parameters; and a display module configured to present the one or more personalized secondary parameters to the user for the user to monitor the user's health condition.

* * * * *